United States Patent [19]

Magiera et al.

[11] 4,231,968
[45] Nov. 4, 1980

[54] STABILIZATION OF 1,1,1-TRICHLOROETHANE

[75] Inventors: Leonhardt Magiera; Raban Grundmann, both of Marl; Dieter Krockenberger, Haltern, all of Fed. Rep. of Germany

[73] Assignee: Chemische Werke Huls Aktiengesellschaft, Marl, Fed. Rep. of Germany

[21] Appl. No.: 5,624

[22] Filed: Jan. 22, 1979

[30] Foreign Application Priority Data

Jan. 27, 1978 [DE] Fed. Rep. of Germany ....... 2803529

[51] Int. Cl.³ ............................................. C07C 17/42
[52] U.S. Cl. ..................................... 570/109; 570/111; 570/110; 570/116; 570/118
[58] Field of Search .................................. 260/652.5 R

[56] References Cited

U.S. PATENT DOCUMENTS

| | | | |
|---|---|---|---|
| 3,499,047 | 3/1970 | Cormany et al. | 260/652.5 R |
| 3,535,392 | 10/1970 | Cormany et al. | 260/652.5 R |
| 3,767,585 | 10/1973 | Sawabe et al. | 260/652.5 R X |
| 4,062,901 | 12/1977 | Lolivier et al. | 260/652.5 R |
| 4,108,910 | 8/1978 | Godfrord et al. | 260/652.5 R |

FOREIGN PATENT DOCUMENTS 49-37633 10/1974 Japan ................................ 260/652.5 R

OTHER PUBLICATIONS

Chemical Abstracts 60, 12243b (1964).
Chemical Abstracts 77, 100730w (1972).
Chemical Abstracts 84, 58595g (1976).
Chemical Abstracts 57, 12317f (1962).

*Primary Examiner*—Helen M. S. Sneed
*Attorney, Agent, or Firm*—Millen & White

[57] ABSTRACT

Addition of 0.2–2 weight % of 2-methyl-2,3-epoxy-propanol-(1), and preferably also 0.2–2% of methyl tert-butyl ether, produces highly stabilized 1,1,1-trichloroethane.

9 Claims, No Drawings

STABILIZATION OF 1,1,1-TRICHLOROETHANE

BACKGROUND OF THE INVENTION

It is known that chlorinated hydrocarbons used for degreasing metals, dry cleaning, and other purposes, decompose upon contact with metal surfaces and corrode them.

One such hydrocarbon, 1,1,1-trichloroethane is being used to an increasing extent because of its good solvent properties together with low toxicity and good ecological properties. However, it decomposes quite easily. Thus, for industrial use, 1,1,1-trichloroethane is provided with stabilizers.

Stabilized mixtures which contain, inter alia, dioxane, nitromethane, acrylonitrile, or epoxybutane as components, are widely used (e.g. DE-PS No. 11 73 306). Satisfactory stabilization can be fully atained with such stabilizer mixtures. But in order to obtain a satisfactory effect, these conventional, stabilizing ingredients must generally be used as a multiple-component mixture and in rather large amounts. Furthermore, recent research has shown that the utilization of dioxane and acrylonitrile entails danger to health so that a replacement for these substances is vitally necessary.

SUMMARY OF THE INVENTION

Accordingly, it is an object of this invention to provide stabilizers for 1,1,1-trichloroethane which pose no environmental hazards and which can be used effectively in relatively small amounts.

Upon further study of the specification and appended claims, further objects and advantages of this invention will become apparent to those skilled in the art.

These objects have been attained by using as a stabilizer for 1,1,1-trichloroethane a stabilizing amount, preferably 0.2–2%, most preferably 0.4–1%, by weight of 2-methyl-2,3-epoxypropanol-(1). Mixtures which also contain 0.2–2%, preferably 0.5–2%, by weight of methyl tert-butyl ether produce especially good stabilizing effects. The 1,1,1-trichloroethane should especially contain 0.4–1% by weight of 2-methyl-2,3-epoxypropanol-(1) and 0.5–2% by weight of methyl tert-butyl ether.

Amounts smaller than those specific ones mentioned above do display some stabilizing effect. However, in practice, in order to ensure effective stabilization, at least the aforementioned minimum quantities are used. Amounts larger than those listed are not damaging; however, they result in only a slight additional stabilizing action.

The stabilizers of the present invention can also be utilized together with any other conventional stabilizers. Thus, 0.5 to 1.5% by weight of nitromethane and, independently or in conjunction therewith, as additional acid acceptors, 0.5 to 1.5% by weight of 1,2-epoxybutane and 0.001 to 0.01% by weight of an amine, such as diisopropylamine or N-methyl morpholine, can also be satisfactorily employed. The 2-methyl-2,3-epoxypropanol-(1) and methyl tert-butyl ether content of the mixture can be lowered in this manner so that the total amount of all stabilizers in the 1,1,1-trichloroethane in no way needs to exceed the quantity of 4% by weight. Preferably, the amount of 2-methyl-2,3-epoxypropanol-(1) in such multicomponent mixtures is 0.4–1.5%, at least 0.2%, and of methyl tert-butyl ether is 0.5–1.5%, at least 0.2%.

Other useful, additional stabilizers include epoxypropane, nitroethane, acetonitrile, acrylonitrile (the use of which, however, is dangerous to health), isopropanol, tert-butanol, tert-amyl alcohol, dioxane (see comment on acrylonitrile), dimethoxy ethane, trioxane, dioxolane, 2-methylbutenol, 2-metylbutynol, orthoformic acid ester, N-alkyl pyrrole, isopropyl nitrate, methyl ethyl ketone, methyl acetate, ethylacetate and toluene. The addition of one of these or similar compounds may be desirable in view of the load factor and the end use of the solvent. Selection of such additional stabilizers and their amounts may be accomplished using conventional considerations and/or routine experimentation. Generally, 0.5–1.5% of any such additional stabilizer will be employed. However, preferred additional stabilizers are the above-mentioned nitromethane, epoxybutane, N-methyl morpholine, and diisopropylamine.

The individual components of the stabilized mixtures are readily available. Preferably, technical or solvent grade reagents are employed. The stabilized mixtures are used in accordance with the known procedures employed in conjunction with conventional mixtures of 1,1,1-trichloroethane for a given end use.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

To assess the stabilizing effect, 1,1,1-trichloroethane was washed neutral with a soda solution and water and was freshly distilled. The iron corrosion test and the aluminum boiling test were subsequently carried out as follows:

A. Iron Corrosion Test 150 cc of 1,1,1-trichloroethane and 1.5 cc of water were placed into a 300 cc Erlenmeyer flask equipped with a reflux condenser. An iron strip (1 × 10 × 100 mm) was suspended in the reflux condenser; another iron strip of the same dimensions was placed in such a way that it was half-submerged in the solvent. The solvent was heated to reflux temperature and exposed to a 60 watt light bulb, while oxygen was passed through at a velocity of 100 bubbles per minute. Visual observations were made of how much time had passed until the first corrosion occurred, recognizable as dot-like veins on the metal surface. Moreover, the total operating time possible until severe corrosion occurred was determined. This time was taken as that when the dot-like veins ran together into reddish-brown coatings covering approximately one-third of the sample surface. The experiment was ended after 72 hours.

B. Aluminum Boiling Test

A specific amount of 1,1,1-trichloroethane was separated by distillation (without fractionation) into three equal parts.

100 cc of the three fractions were respectively mixed with 100 ml of toluene, 18 g of Al flakes, 0.7 g of $AlCl_3$, and 1 g of zinc stearate, and heated for 24 hours at reflux temperature.

The test is passed when no exothermic reaction takes place in any of the three fractions. In addition, the color of the solvent is evaluated.

EXAMPLES 1 THROUGH 10

Iron Corrosion Test, Individual Components

| Example | CONTENT [%] | Time to Beginning of Corrosion [h] | Total Operating Time [h] |
|---|---|---|---|
| 1 | 1 Nitromethane (NM) | 2 | 3 |
| 2 | 4 NM | 4 | 6 |
| 3 | 1 Acrylonitrile (AN) | 1 | 3 |
| 4 | 4 AN | 3 | 6 |
| 5 | 4 1,2-Epoxybutane (EB) | 1 | 1 |
| 6 | 4 2-Methylbutyn-3-ol | 1 | 6 |
| 7 | 1 2-Methyl-2,3-epoxypropanol (MEP) | 24 | 48 |
| 8 | 4 MEP | 42 | >72 |
| 9 | 0.5 MEP | 10 | 32 |
| 10 | 4 2,3-Epoxypropanol (EP)^xx | 4 | 6 |

^xx The mixture is cloudy and separates into two phases when left to stand.

Mixtures 7 through 9 are those according to the invention. They demonstrate the excellent, corrosion-inhibiting effect of 2-methyl-2,3-epoxypropanol (MEP).

EXAMPLES 11 THROUGH 24

Iron Corrosion Test, Mixtures of Components

| Example | Content [%] | Time to Beginning of Corrosion [h] | Total Operating Time [h] |
|---|---|---|---|
| 11 | 1 NM + 1 EB + 2 Dioxane (DI) | 2 | 6 |
| 12 | 2 NM + EB + 1 DI | 1.5 | 6 |
| 13 | 1 NM + 1 EB + 1 DI + 1 AN | 4 | 6 |
| 14 | 1 EB + 1 DI + 2 AN | 10 | 30 |
| 15 | 1 NM + 1 EB + 1 MEP + 1 Methyl tert-butyl ether (MTB) | 48 | >72 |
| 16 | 1 NM + 1 EB + 0.5 MEP + 1 MTB + 0.003 Diisopropylamine (DIPA) | 72 | >72 |
| 17 | 1 NM + EB + 0.5 MEP + 0.5 MTB + 0.003 N-Methyl morpholine (NMM) | 40 | >72 |
| 18 | 1 NM + 1 MEP | 36 | 50 |
| 19 | 1 EB + 1 MEP | 24 | 48 |
| 20 | 1 DI + 1 MEP | 24 | 50 |
| 21 | 1 MTB + 1 MEP | 40 | >72 |
| 22 | 2 MTB + 2 MEP | >72 | >72 |
| 23 | 0.5 MTB + 0.5 MEP | 20 | 42 |
| 24 | 1 MTB + 1 EP | 2 | 6 |

Examples 15 to 20 are those according to the invention; they demonstrate the considerable improvement in stability due to the use of 2-methyl-2,3-epoxypropanol (MEP). The combination of MEP+MTB is quite especially advantageous.

EXAMPLES 25 THROUGH 32

Aluminum Boiling Test, Mixture of Components

The relatively strict aluminum boiling test was not passed by mixtures of 1,1,1-trichloroethane and one individual component (tested up to 4% addition). The following mixtures were also tested.

| Example | Content [%] | Result^x |
|---|---|---|
| 25 | 2 NM + 2 DI | (−) |
| 26 | 2 NM + 2 EB | (−) |
| 27 | 2 NM + 1 DI + 1 EB | (−) |
| 28 | 2 NM + 2 MEP | (+) |
| 29 | 2 NM + 1 MEP + 1 MTB | (+) |
| 30 | 1 NM + 1 MEP + 1 MTB + 1 EB | (+) |
| 31 | 1 NM + 0.5 MEP + 1 MTB + 1.5 EB | (+) |
| 32 | 1 NM + 1 MEP + 0.5 MTB + 1.5 EB | (+) |

^x (−) = failed, exothermic reaction with black coloration
(+) = passed, no reaction In comparison to Experiments 25 to 27, in this test Experiments 28 and 29 show the superior stabilizer effect of 2-methyl-2,3-epoxypropanol (MEP) or a mixture of 2-methyl-2,3-epoxypropanol and methyl tert-butyl ether (MTB).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Stabilized 1,1,1-trichloroethane containing a stabilizer, the stabilizer consisting essentially of (a) 0.2–2% by weight of the total mixture of 2-methyl-2,3-epoxypropanol-(1); (b) 0.2–2% by weight of the total mixture of 2-methyl-2,3-epoxypropanol-(1) and 0.2–2% by weight of the total mixture of methyl tert-butyl ether; or (c) a mixture of either (a) or (b) and 0.5–1.5% by weight of the total mixture of nitromethane, 0.5–1.5% by weight of the total mixture of 1,2-epoxybutane or 0.001 to 0.01% by weight of the total mixture of diisopropylamine or N-methyl morpholine.

2. The stabilized 1,1,1-trichloroethane of claim 1, wherein the stabilizer is 0.2–2% by weight of the total mixture of 2-methyl-2,3-epoxypropanol-(1).

3. The stabilized 1,1,1-trichloroethane of claim 2 wherein the amount of 2-methyl-2,3-epoxypropanol-(1) is 0.4–1%.

4. The stabilized 1,1,1-trichloroethane of claim 1 wherein the stabilizer is (b).

5. The stabilized 1,1,1-trichloroethane of claim 1 wherein the stabilizer is (b), the amount of 2-methyl-2,3-epoxypropanol-(1) is 0.4–1% and the amount of methyl tert-butyl ether is 0.5–2%.

6. The stabilized 1,1,1-trichloroethane of claim 1 wherein the stabilizer is 0.5–1.5% by weight of nitromethane, 0.5–1.5% by weight of 1,2-epoxybutane or 0.001 to 0.01% by weight of diisopropylamine or N-methyl morpholine and 0.2–2% by weight of the total mixture of 2-methyl-2,3-epoxypropanol-(1).

7. The stabilized 1,1,1-trichloroethane of claim 1 wherein the stabilizer is 0.5–1.5% by weight of the total mixture of 1,2-epoxybutane or 0.001 to 0.01% by weight of the total mixture of diisopropylamine or N-methyl morpholine and 0.2–2% by weight of the total mixture of 2-methyl-2,3-epoxypropanol-(1) and 0.2–2% by weight of the total mixture of methyl tert-butyl ether.

8. A method of stabilizing 1,1,1-trichloroethane against decomposition upon contact with metal surfaces and of minimizing the corrosion of metal surfaces caused by contact with 1,1,1-trichloroethane which comprises adding to 1,1,1-trichloroethane a stabilizer consisting essentially of (a) 0.2–2% by weight of the total mixture of 2-methyl-2,3-epoxypropanol-(1); (b) 0.2–2% by weight of the total mixture of 2-methyl-2,3-epoxypropanol and 0.2–2% by weight of the total mixture of methyl tert-butyl ether; or (c) a mixture of ether (a) or (b) and 0.5–1.5% by weight of the total mixture of nitromethane, 0.5–1.5% by weight of the total mixture of 1,2-epoxybutane or 0.001 to 0.01% by weight of the total mixture of diisopropylamine or N-methyl morpholine.

9. Stabilized 1,1,1-trichloroethane containing a stabilizer consisting essentially of a stabilizing amount of 2-methyl-2,3-epoxypropanol-(1).

* * * * *

UNITED STATES PATENT AND TRADEMARK OFFICE
CERTIFICATE OF CORRECTION

PATENT NO. : 4,231,968
DATED : November 4, 1980
INVENTOR(S) : Leonhardt Magiera et al It is certified that error appears in the above—identified patent and that said Letters Patent is hereby corrected as shown below:

Column 5, line 5: reads "ture of methyl tert-butyl ether; or (c) a mixture of ether"

should read -- ture of methyl tert-butyl ether; or (c) a mixture of either -- .

Signed and Sealed this

Tenth Day of February 1981

[SEAL]

Attest:

Attesting Officer

RENE D. TEGTMEYER

Acting Commissioner of Patents and Trademarks